United States Patent [19]

Mahutte et al.

[11] Patent Number: 4,949,724

[45] Date of Patent: Aug. 21, 1990

[54] METHOD AND APPARATUS FOR CONTINUOUS MEASUREMENT OF CARDIAC OUTPUT

[76] Inventors: Cornelis K. Mahutte, 1371 Gwen; Pieter Halter, 11111 Yarmouth, both of Santa Ana, Calif. 92705

[21] Appl. No.: 289,969

[22] Filed: Dec. 23, 1988

[51] Int. Cl.$^5$ ............................................. A61B 5/028
[52] U.S. Cl. .................................................. 128/713
[58] Field of Search ............... 128/713, 670, 671, 691, 128/719, 633, 634

[56] References Cited

U.S. PATENT DOCUMENTS

4,201,222  5/1980  Haase .................................. 128/634

OTHER PUBLICATIONS

Datascope Technical Reference 10/27/83.
"Continuous Fick Cardiac Output Compared to Continuous Pulmonary Artery Electromagnetic Flow Measurement in Pigs", Anesthesiology, 66:805–809, 1987, Gerald Davies.
Blanch L. et al., Accuracy of an Indirect Carbon Dioxide Fick Method in Determination of the Cardiac Output in Critically Ill Mechanically Ventilated Patients. Intens Care Med 14, 131, 1988.
Ultman, J. C. et al., Analysis of Error in the Determination of Respiratory Gas Exchange at Varying $F_iO_2$. J Appl Physiol 50, 210, 1981.
Van Lanschot, J. Jan B. et al. Accuracy of Intermittent Metabolic Gas Exchange Recordings Extrapolated for Diurnal Variation, Crit. Care Med, vol. 16, No. 8, Aug. 1988, pp. 737–741.
Capek, John M. et al., Noninvasive Measurement of Cardiac Output Using Partial $CO_2$ Rebreathing, IEEE Transactions on Biomedical Eng., vol. 35, No. 9, Sep. 1988, pp. 653–661.
Davies, G. G. et al., Continuous Fick Cardiac Output Compared to Dilution Cardiac Output., Crit. Care Med 14, 881, 1986.
Ehlers, K. C. et al., Cardiac Output Measurements. A Review of Current Techniques and Research. Ann Biomed Eng 14, 219, 1986.
Hankeln K. et al., Continuous, On-Line, Real-Time Measurement of Cardiac Output and Derived Cardiorespiratory Variables in the Critically Ill. Crit. Care Med 13, 1071, 1985.
Tachimori Y. et al., On-Line Monitoring System for Continuous and Real-Time Cardiac Output. Crit. Care Med (Abstract) 14, 401, 1986.
Davis, C. C. et al., Measurements of Cardiac Output in Seriously Ill Patients Using a $CO_2$ Rebreathing Method. Chest 73, 167, 1978.

*Primary Examiner*—Lee S. Cohen
*Assistant Examiner*—S. Getzow
*Attorney, Agent, or Firm*—Spensley Horn Jubas & Lubitz

[57] ABSTRACT

A method of continuously monitoring cardiac output of a patient includes the step of determining a value of a cardiac output constant which is assumed to remain stable over the period of interest and is determined as a function of values of various measured parameters of the patient. These values may include thermodilution cardiac output, carbon dioxide production, arterial and mixed venous oxygen saturation and hemoglobin. Thereafter, cardiac output is continuously determined employing the calculated cardiac output constant and monitored values of carbon dioxide production and arterial and mixed venous oxygen saturation. Oxygen transport may also be monitored on a continuous basis.

33 Claims, 2 Drawing Sheets

METHOD AND APPARATUS FOR CONTINUOUS MEASUREMENT OF CARDIAC OUTPUT

BACKGROUND OF THE INVENTION

1. Field of the Invention

The present invention relates to the continuous measurement or monitoring of the cardiac output of the human body. Cardiac output is the volume of blood ejected by the heart per unit time. It is a useful measurement in that it can be used to evaluate overall cardiac status in critically ill patients, patients with suspected cardiovascular and pulmonary disease, and high risk patients undergoing surgery. The present invention also relates to continuous monitoring of oxygen transport. Oxygen transport is the volume of oxygen transported from the heart and lungs to the body per unit time. It is useful to assess the cardiorespiratory status of the above patients.

2. Description of the Prior Art

Cardiac output has been measured by a number of different methods. Several methods are described in *Cardiac Output Measurements. A review Of Current Techniques And Research*, by Ehlers et al. in the *Annals Of Biomedical Engineering*, Vol. 14, pp. 219-239, 1986. This publication discusses both "intermittent" cardiac output measurements for obtaining a single measurement and "continuous" measurements in which various patient parameters are continuously monitored and cardiac output calculated on a regular and repeating basis. Although high accuracy can be obtained with certain intermittent measurement techniques, it is very desirable to be able to provide continuous information regarding cardiac output. Currently, the most popular technique for measuring cardiac output intermittently is via an indicator dilution method, and particularly thermodilution. In indicator dilution techniques, a predetermined amount of substance is introduced at a single point in the bloodstream and analyzed at a point downstream to obtain a time dilution curve. The average volume flow is inversely proportional to the integrated area under the dilution curve. In the thermodilution method, the indicator is a temperature change of the blood. The temperature change is typically produced by injecting cold saline through a catheter into the right atrium. This results in a cooling of the blood, which is measured at a downstream location with the same catheter to produce a thermodilution curve. Cardiac output can then be determined. This technique employs a catheter with a thermistor at the tip.

Other methods of cardiac output measurement are based upon the Fick principle. According to this principle, the rate of uptake or release of a substance to or from blood at the lung is equal to the blood flow past the lung and the content difference of the substance at each side of the lung. This can be expressed by the equation:

$$\text{Uptake} = Q(c_2 - c_1),$$

where Q is the blood flow (cardiac output), $c_2$ the content of the substance leaving from the lung and $c_1$ the content of the substance coming to the lung. Applying this relationship to oxygen yields:

$$Q = VO_2/(c_aO_2 - c_vO_2), \quad (1)$$

where $VO_2$ is the volume of oxygen inspired per unit time and $c_aO_2$ and $c_vO_2$ are respectively the arterial and mixed venous oxygen contents. Applying the relationship to carbon dioxide yields:

$$Q = VCO_2/(c_vCO_2 - c_aCO_2), \quad (2)$$

where $VCO_2$ is the volume of carbon dioxide produced by the patient per unit time and $c_vCO_2$ and $c_aCO_2$ are respectively the mixed venous and arterial carbon dioxide contents. Determination of $VO_2$ and $VCO_2$ require a volume measurement (e.g., via integration of a flow signal or via a rotameter) and a fractional concentration measurement (e.g., via mass spectrometer or gas analyzer (infrared or polarographic)).

The Fick method is most commonly used with oxygen as the analyzed substance. Equation $(_1)$ has been used to obtain intermittent measurements of Q. Via indwelling catheters, arterial and venous blood samples were obtained and these samples were analyzed on a blood gas analyzer to obtain the oxygen saturation ($SO_2$) and the partial pressure of oxygen ($PO_2$). Arterial and venous oxygen contents were then calculated from the formula:

$$cO_2 = 1.34 \cdot Hgb \cdot SO_2 + 0.0031 \cdot PO_2, \quad (3)$$

where Hgb is the hemoglobin in gm/100ml of the patient, $SO_2$ is in percent, $cO_2$ is in ml of $O_2$/100ml of blood, and 1.34 is a constant in ml/gm (other values of this constant, e.g., 1.36 and 1.39 have also appeared in the literature). The above approach only yields intermittent measurements and is also cumbersome. Therefore, it is typically not used in critically ill patients.

The dissolved oxygen ($0.0031 \cdot PO_2$) in equation (3) is generally negligible so that equation (1) can be simplified to:

$$Q = VO_2/(13.4 \cdot Hgb \cdot (S_aO_2 - S_vO_2)) \quad (4)$$

where Q is in l/min, $VO_2$ in ml/min, Hgb in gm/100ml and S in percent. $S_aO_2$ can be measured continuously via an oximeter (pulse, transmission or indwelling type). Similarly, $S_vO_2$ can be measured continuously via reflectance oximetry and a fiberoptic pulmonary artery (right heart) catheter. Several systems have been developed to continuously monitor cardiac output via continuous measurement of $VO_2$, $S_aO_2$ and $S_vO_2$. Such methods are described in Hankeln, et al. *Continuous, On-line, Real-Time Measurement of Cardiac Output and Derived Cardiorespiratory Variables in the Critically Ill.* Crit. Care Med 13, 1071, 1985; Davies, et al. *Continuous Fick Cardiac Output Compared to Dilution Cardiac Output.* Crit. Care Med 14, 881, 1986; and Tachimori, et al. *On-line Monitoring System for Continuous and Real-Time Cardiac Output.* Crit Care Med (Abstract) 14, 401, 1986. The methods described provide fairly good results;

however, oxygen Fick methods all have the common drawback that it is difficult to measure the body's rate of oxygen uptake accurately. This is particularly so when the patient is inspiring a high concentration of oxygen (FIO2), as occurs frequently in critically ill patients. In addition, FIO2 can vary from breath to breath in patients on ventilators (this occurs because of inaccuracies in the internal blender or pressure fluctuations in the oxygen and air supply). VO2 measurement is therefore difficult in ventilator dependent patients unless a blender external to the ventilator or calibrated gases from an external tank are used. Furthermore, patients may be on various modes of ventilation such as flow-by, where part of the oxygen bypasses the patient's mouth. In this situation, complicated valving is required to separate the patient's exhaled gas from the flow-by gas. It is therefore difficult to provide a universally applicable system for VO2 measurement.

The difficulty of VO2 measurement at high oxygen concentration is recognized in the Davies et al publication and is theoretically discussed in Ultman, et al., *Analysis of Error in the Determination of Respiratory Gas Exchange at Varying $F_IO_2$*, J Appl Physiol 50, 210, 1981. The Davies publication mentions approximating the VO2 by measuring carbon dioxide output (VCO2) and dividing it by an assumed respiratory quotient RQ. This method has the potential disadvantage that the assumed value of the respiratory quotient of the patient may be incorrect.

The Fick method has also been applied to carbon dioxide employing equation (2) to obtain intermittent cardiac output. The $c_vCO_2$ is usually estimated from the partial pressure of carbon dioxide ($P_vCO_2$). The latter may be obtained indirectly by breath holding or more popularly by rebreathing. Such methods are described in Davis, C.C., et al. *Measurements of Cardiac Output in Seriously Ill Patients Using a CO Rebreathing Method.* Chest 73, 167, 1978; and Blanch, et al., *Accuracy of an Indirect Carbon Dioxide Fick Method in Determination of the Cardiac Output in Critically Ill Mechanically Ventilated Patients,* Int. Care Med 14, 131, 1988. A major disadvantage of this method is that it yields only intermittent values of Q since the partial pressure of carbon dioxide is estimated via rebreathing. More recently, a partial rebreathing method that does not require monitoring of $P_vCO_2$ has been used in dogs (Capek, et al., *Noninvasive Measurement of Cardiac Output Using Partial CO2 Rebreathing.* IEEE Trans. Biomed. Eng. 35, 653, 1988). This method is also intermittent and it is unlikely that it can be easily applied to patients with lung disease.

SUMMARY OF THE INVENTION

The present invention is directed to a method and apparatus for continuously monitoring cardiac output by utilizing a modified Fick equation. In order to eliminate the inaccuracies associated with monitoring the rate of uptake of oxygen, however, VO2 in the oxygen Fick equation is replaced by VCO2 divided by a constant representative of the gas exchange ratio of a patient. This ratio is assumed to remain constant over the measurement period of interest The value of the constant is determined for the patient by initially measuring at least one patient parameter and making a determination of the constant based upon the measured parameter. In one embodiment, an initial cardiac output determination employing a technique such as thermodilution is performed and initial values of arterial and mixed venous oxygen saturation and CO2 production for the patient are obtained. The obtained values are inserted into the modified Fick equation in order to obtain a value of a constant, referred to as a "cardiac output constant". Subsequently, the volume of carbon dioxide expired by the patient and mixed venous oxygen saturation content are continuously monitored, and cardiac output is calculated in real time from the current monitored values and the previously determined cardiac output constant. The initial arterial oxygen saturation value may be used in the modified Fick equation for certain patients in which arterial oxygen saturation remains substantially constant. For other patients, the arterial oxygen saturation content is continuously monitored and the current value inserted into the modified Fick equation. Hemoglobin may be monitored on an intermittent or continuous basis or may be assumed to be a constant value and be included in the cardiac output constant. Real time output can be combined with the simultaneously obtained oxygen saturation to yield real time oxygen transported to the tissues. The invention can provide significant improvements in continuous cardiac output and oxygen transport measurement by relying upon measurements of carbon dioxide production rather than oxygen consumption.

BRIEF DESCRIPTION OF THE DRAWINGS

The invention will be described with reference to the accompanying drawings, wherein.

DESCRIPTION OF THE PREFERRED EMBODIMENTS

Figure 1:
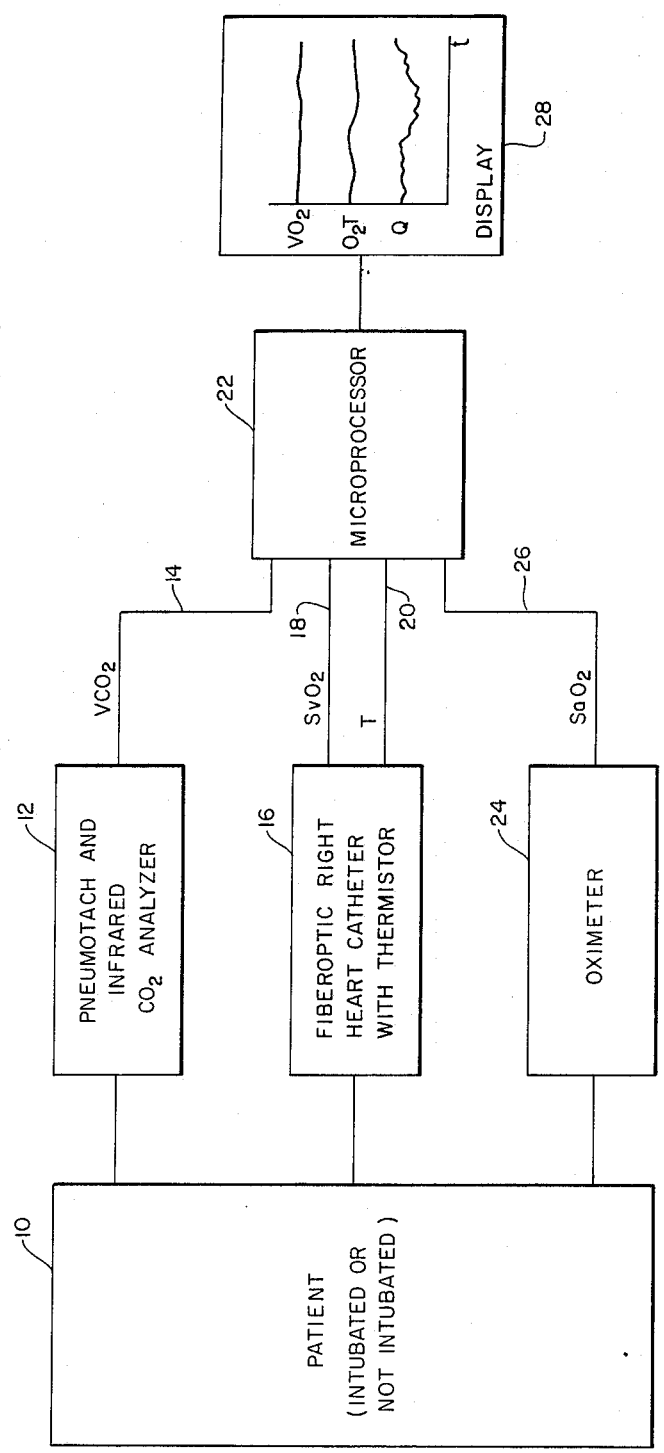
FIG. 1 is a block diagram of the present invention.

The following description is of the best presently contemplated mode of carrying out the invention. This description is made for the purpose of illustrating the general principles of the invention and is not to be taken in a limiting sense. The scope of the invention is best determined by reference to the accompanying claims.

As discussed above, the oxygen Fick equation is represented in general form by the following:

$$Q = VO_2/(c_aO_2 - c_vO_2). \quad (1)$$

By ignoring the dissolved oxygen content expressed in equation (3), the above oxygen Fick equation can be represented as:

$$Q = VO_2/(13.4 \cdot Hgb \cdot (S_aO_2 - S_vO_2)) \quad (4)$$

The present invention relies on the postulate/observation that during the steady state the gas exchange ratio, R, for carbon dioxide and oxygen is constant:

$$R = VCO_2/VO_2 = \text{constant} \quad (5)$$

The value of this constant depends primarily on the fuel mixture (e.g., fat, protein or carbohydrate) that the body is metabolizing. The present invention is based upon the assumption that R will not vary significantly over the time period of interest (e.g., a number of hours). Research has provided evidence that this is valid over 24 hours at least with respect to critically ill patients (see. e.g. van Lanschot, et al. *Accuracy of Intermittent Metabolic Gas Exchange Recordings Extrapolated for Dinural Variation.* Crit. Care Med. 16, 737, 1988.) R may therefore be considered constant and $VO_2$ in equation (4) may be replaced by $VCO_2/R$. This yields the following:

$$Q = VCO_2/(13.4 \cdot Hgb \cdot R \cdot (S_aO_2 - S_vO_2)) \quad (6)$$

This is of the form:

$$Q = VCO_2/(k \cdot (S_aO_2 - S_vO_2)), \quad (7)$$

where k is a constant (k = 13.4 · Hgb · R) and the variables are functions of time.

From equation (7), Q can be determined and measured continuously if k is known and if $VCO_2$, $S_aO_2$ and $S_vO_2$ are continuously monitored. In the preferred embodiment of the present invention, k is determined by making an initial cardiac output determination with another technique, such as thermodilution. At a time zero, Q, $VCO_2$, $S_aO_2$, and $S_vO_2$ are measured. A hemoglobin measurement may also be made from a blood sample of the patient. Substituting these initial values of Q, $VCO_2$, $S_aO_2$ and $S_vO_2$ in equation (7) yields k. Q may thereafter be continuously determined by monitoring $VCO_2$, $S_aO_2$ and $S_vO_2$.

Referring to FIG. 1, a patient is indicated at 10. Various continuous monitoring devices are coupled to the patient in order to facilitate the continuous cardiac output measurement of the present invention. Each of these devices is commercially available. The volume of carbon dioxide expired by the patient is monitored by means of a volumetric analyzer 12 which includes, for example, a pneumotach and infrared $CO_2$ analyzer along with appropriate processing circuitry. An output signal is provided on line 14 representative of the volume of carbon dioxide expired by the patient per unit time (e.g., ml/min). This measurement is averaged over time intervals sufficient to filter out rapid fluctuations and thus provides an accurate representation of volume of carbon dioxide expired by the patient. The unit 12 may, for example, be comprised of a Beckman MMC Horizon System which provides an output of carbon dioxide production in ml/min. Such an output is also provided by a Waters Instruments, Inc. MRM-6000 metabolic analyzer.

A fiberoptic pulmonary (right heart) catheter 16 including a thermistor is employed to monitor mixed venous oxygen saturation and to perform the initial thermodilution cardiac output measurements. Several fiberoptic right heart catheters are commercially available, and may include circuitry to provide an output signal representative of mixed venous oxygen saturation $S_vO_2$, expressed as a percentage. This output is indicated on line 18 in FIG. 1. An Oximetrix Model IX catheter providing a continuous output signal representative of $S_vO_2$ may be employed. This unit includes a catheter and oximetry processor (Oximetrix 3 $SO_2$/cardiac output computer, Abbott Labs, Mountain View, CA.) to provide the $S_vO_2$ signal. Other units, such as an Edwards $S_vO_2$/cardiac output unit (SAT 2, Baxter Edwards, Irvine, CA.) with an Edwards venous oximetry catheter, could also be used.

The right heart catheter 16 includes a thermistor to provide a temperature signal for use in calculating an initial cardiac output by means of the thermodilution technique. The temperature output of the thermistor is provided on line 20 to a microprocessor system 22 which is employed to calculate thermodilution cardiac output $Q_{TD}$ by employing a known thermodilution cardiac output equation (such as that disclosed in Ehlers et al, supra). The thermodilution cardiac output as determined by the microprocessor 22 is employed to determine the cardiac output constant as discussed below. (It should be noted that the catheter unit may include its own processing circuitry, in which case the output to the processor 22 would be a calculated value of $Q_{TD}$ rather than temperature.)

An oximeter 24, which may be a pulse, transmission, reflectance or indwelling type, is employed to monitor arterial oxygen saturation of the patient 10. The oximeter 24 provides an output signal on line 26 indicative of arterial saturation percentage. In one embodiment, an Ohmeda Biox 3740 pulse oximeter is employed to provide the $S_aO_2$ signal.

Thus, the microprocessor 22 receives continuous signals indicating the value of $VCO_2$, $S_vO_2$ and $S_aO_2$ on lines 14, 18 and 26, respectively. In addition, temperature measurements are received on line 20 to facilitate the initial thermodilution cardiac output determination (and possible subsequent determinations if updating is desired).

Figure 2:
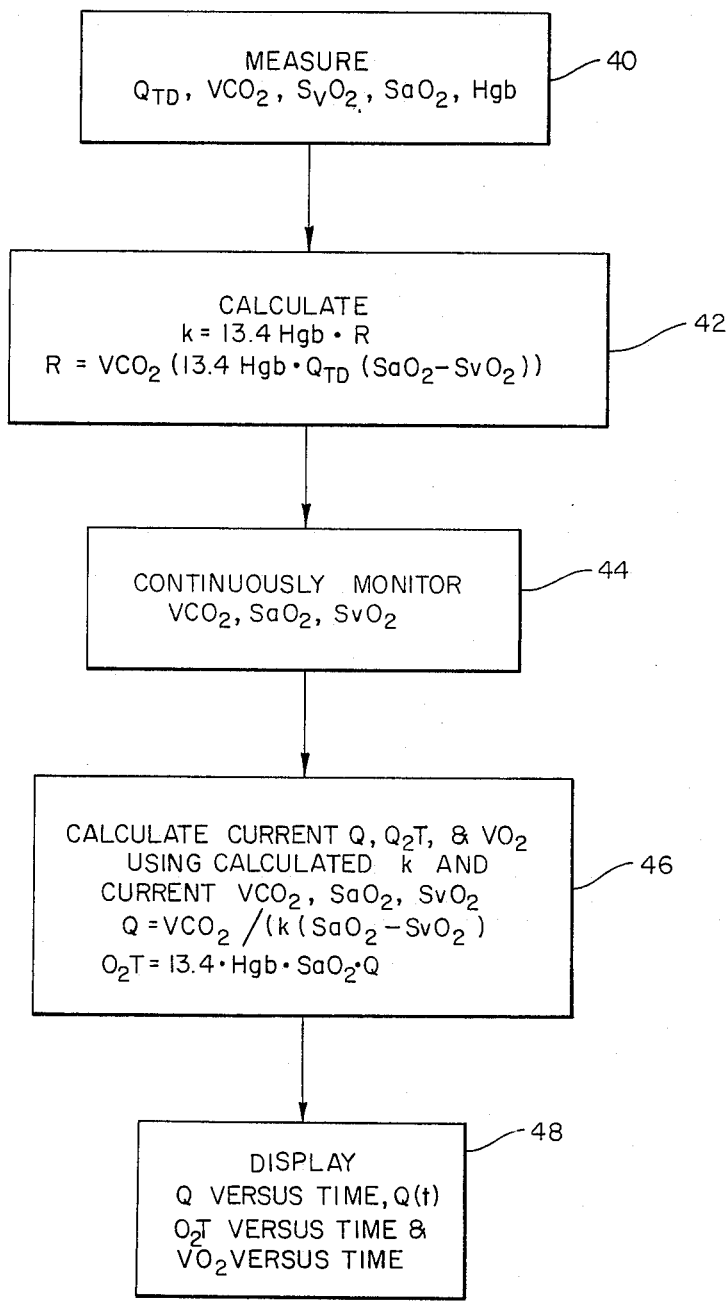
FIG. 2 is a block diagram illustrating the method of the present invention.

The method for continuously measuring cardiac output in conjunction with the system of FIG. 1 is illustrated in FIG. 2. When it is desired to begin measuring cardiac output, several thermodilution cardiac outputs $Q_{TD}$ are obtained by employing the known thermodilution technique. An average $Q_{TD}$ is then determined. Initial values of $VCO_2$, $S_vO_2$ and $S_aO_2$ are obtained from the units 12, 16 and 24, respectively. In addition, a value of the patient's hemoglobin Hgb is obtained by blood sample analysis. These initial measurements are indicated at 40 in FIG. 2. Once the initial values are obtained, the value of R in equation (6) and the value of k in equation (7) can be calculated by the microprocessor 22. This is indicated at box 42 in FIG. 2.

Once the value of k has been determined, continuous determination of cardiac output is facilitated by monitoring the $VCO_2$, $S_vO_2$ and $S_aO_2$ signals on lines 14, 18 and 26. That is, the microprocessor 22 can continuously calculate Q based upon equation (7) employing the previously calculated value of k. This is indicated at boxes 44 and 46 of FIG. 2. The calculated value of Q may be displayed over time (Q(t)) by means of a display 28 shown in FIG. 1 and indicated at Box 48 in FIG. 2. In this embodiment, it is assumed that the value of k (which includes R and Hgb) for a patient will remain substantially constant for the time period of interest (e.g., a 24 hour period), and it is therefore sufficient to perform only one thermodilution cardiac output determination (typically the average of several measurements closely spaced in time) at the beginning of this time period in order to calculate k. However, k and R may be repeatedly updated by performing the initialization procedure in step 40 (FIG. 2) at any desired times (e.g., each 4 hours). During these intervals Q(t) may be displayed as described above and in FIG. 2.

The use of the measured values of $VCO_2$, $S_vO_2$ and $S_aO_2$ to calculate k and subsequently calculate Q has the further advantage that any instrumentation offsets associated with these measurements are compensated for in the calculated value of k. It is therefore preferable to employ these parameters in determining k. However, the invention is not so limited. R or k may be determined by other methods. For example, in addition to the $VCO_2$ measurement obtained by the unit 12, $VO_2$ may be measured (by using the Beckman MMC Horizon System, for example) and R calculated from equation (5). Arterial and venous blood sampling may also be used to determine R. Combining equations (1) and (2) yields:

$$R = (c_v - c_aCO_2)/(c_aO_2 - c_vO_2) \quad (8),$$

so that R can be determined from the arterial and venous oxygen and carbon dioxide contents.

Alternatively, $VO_2$ may be calculated via equation (1) from the initial cardiac output measurement Q and measured (e.g., via blood sampling) arterial and venous oxygen contents. Use of this $VO_2$, together with the simultaneously measured $VCO_2$, in equation (5) yields R.

In each implementation of the present invention, at least one initial parameter of the patient is measured and a cardiac output constant is determined. This constant is then used in the modified Fick equation in order to enable continuous measurements of cardiac output to be obtained by monitoring $VCO_2$, $S_vO_2$ and $S_aO_2$ (and Hgb if desired). By enabling measurements to be made based upon carbon dioxide production as opposed to oxygen uptake, accurate and consistent continuous cardiac output measurements may be obtained.

Since R is determined by an initial thermodilution measurement of cardiac output and $CO_2$ production is monitored continuously thereafter, it is possible to employ equation (5) to continuously monitor oxygen uptake, $VO_2$. This value may be calculated by the microprocessor 22 and displayed on the display unit 28. Similarly, oxygen transport of the patient may be calculated in accordance with the following:

$$O_2T = 10.c_aO_2.Q(t) = 13.4Hgb.S_aO_2.Q(t), \quad (9)$$

where $O_2T$ is the oxygen transported by the heart to the body in ml/min. The real time calculated value may be displayed by the unit 28. Other patient parameters, such as oxygen extraction ratio ($VO_2O_2T$) may also be continuously monitored. The initial determination of R and subsequent real time monitoring of $VCO_2$, $S_aO_2$ and $S_vO_2$ thus facilitates monitoring of various parameters in addition to cardiac output.

When employing equation (7) to determine Q, the patient's hemoglobin is assumed to remain constant and is therefore included in the value of the calculated cardiac output constant k. However, more accurate determination of Q is facilitated by treating hemoglobin as a variable and monitoring its value either intermittently or continuously. In this case, the equation for determining cardiac output is as follows:

$$Q = VCO_2/(k'. Hgb . (S_aO_2 - S_vO_2)), \quad (10)$$

where k' is equal to 13.4.R, from equation (6). Values for Hgb are provided to the microprocessor 22 in this embodiment along with the values of $VCO_2$, $S_vO_2$ and $S_aO_2$. The value of the constant k' is then determined (like k) from the initial values of Q, Hgb, $S_aO_2$ and $S_vO_2$. Once k' is determined Q may be monitored in real time from the values of $VCO_2$, Hgb, $S_aO_2$ and $S_vO_2$.

Although k' or R may generally be assumed to remain constant over a 24 hour period, further accuracy in the continuous determination of Q may be obtained by intermittently (e.g., every four hours) recalculating k' or R by, for example, making another thermodilution cardiac output determination or by determining cardiac output via other invasive or non-invasive means. Continuous measurements of Q are then resumed based upon the new value of R. Recalculating k' or R in this manner would also correct for any instrumentation drifts that might have occurred over the time period.

The embodiments described above continuously monitor $S_aO_2$ to obtain a current value for use in the modified Fick equation. However, this is not always necessary. In certain patients, who are well oxygenated and have no lung disease (e.g., cardiac patients) it may not be necessary to continuously monitor $S_aO_2$ since this is a constant (e.g., 96% to 98%). A single initial arterial blood sample will therefore suffice to determine the $S_aO_2$ value for use in the modified Fick equation. In t case, equations 7 and 9 have $S_aO_2$ equal to a constant, and Q can be determined by continuously monitoring $VCO_2$ and $S_vO_2$ once k or k' (together with Hgb) is determined as described above.

What is claimed is:

1. A method of continuous monitoring of the cardiac output of a patient comprising the steps of:
    determining a value of a cardiac output constant for the patient by measuring at least one parameter of the patient and calculating the cardiac output constant as a function of the measured parameter, wherein the cardiac output constant is calculated without employing any assumed ratio between oxygen intake and carbon dioxide production by the patient;
    continuously monitoring carbon dioxide production and mixed venous oxygen saturation of the patient to obtain current values thereof; and
    monitoring cardiac output of the patient over time by calculating a value of cardiac output as a function of the current values of carbon dioxide production and mixed venous oxygen saturation and the previously calculated value of the cardiac output constant.

2. The method of claim 1 including the step of continuously monitoring arterial oxygen saturation of the patient to obtain a current value thereof, wherein the value of cardiac output is calculated as a function of the current value of arterial oxygen saturation and the current values of carbon dioxide production and mixed venous oxygen saturation.

3. The method of claim 2 including the step of monitoring oxygen transport of the patient over time by determining a value thereof as a function of the cardiac output constant and at least one of said current values.

4. The method of claim 3 including the step of displaying a value of oxygen transport over time.

5. The method of claim 1 wherein the cardiac output constant includes an actual gas exchange ratio R of the patient as a component thereof, where R is equal to the ratio of carbon dioxide production of the patient to oxygen intake of the patient.

6. The method of claim 5 wherein the step of determining the value of the cardiac output constant includes the steps of obtaining arterial and venous blood samples from the patient, determining the relative concentrations of oxygen and carbon dioxide in each of the samples and determining the cardiac output constant as a function of the determined concentrations.

7. The method of claim 6 including the step of determining R, wherein R is determined in accordance with the equation $R = (c_v CO_2 - c_a CO_2)/(c_a O_2 - c_v O_2)$, where $c_v CO_2$ and $c_v O_2$ are respectively the carbon dioxide and oxygen contents of the venous blood sample and $c_a CO_2$ and $c_a O_2$ are respectively the carbon dioxide and oxygen contents of the arterial blood sample.

8. The method of claim 5 wherein the step of determining the cardiac output constant includes the step of measuring values of the oxygen intake and carbon dioxide output of the patient, calculating R as a function of the measured values, and calculating the cardiac output constant as a function of the calculated value of R.

9. The method of claim 1 wherein the cardiac output constant includes a value of hemoglobin of the patient as a component thereof.

10. The method of claim 1 including the step of monitoring hemoglobin value of the patient over time and calculating the cardiac output value as a function of the monitored hemoglobin values.

11. The method of claim 1 including the step of displaying the value of cardiac output over time.

12. A method of continuous monitoring of the cardiac output of a patient comprising the steps of:
determining a value of a cardiac output constant for the patient by measuring at least one parameter of the patient and calculating the cardiac output constant as a function of the measured parameter wherein the step of determining the value of the cardiac output constant includes the step of making an initial measurement of cardiac output of the patient by means of a first technique and calculating the constant as a function of the initial value of cardiac output;
continuously monitoring carbon dioxide production and mixed venous oxygen saturation of the patient to obtain current values thereof; and
monitoring cardiac output of the patient over time by calculating a value of cardiac output as a function of the current values of carbon dioxide production and mixed venous oxygen saturation and the previously calculated value of the cardiac output constant.

13. The method of claim 12 including the step of making at least an initial measurement of arterial oxygen saturation of the patient, wherein the step of determining the value of the cardiac output constant includes the step of calculating the constant as a function of the initial value of cardiac output and initial values of carbon dioxide production, arterial oxygen saturation and mixed venous oxygen saturation.

14. The method of claim 13 including the step of determining the value of a respiratory quotient R wherein R is determined substantially in accordance with the equation $R = VCO_2/(13.4 \cdot Hgb \cdot Q \cdot (S_a O_2 - S_v O_2))$ where $VCO_2$ is volume of carbon dioxide exhaled per unit time by the patient, Hgb is hemoglobin of the patient, Q is cardiac output of the patient in volume per unit time as obtained by the initial measurement, $S_a O_2$ is the initial value of arterial oxygen saturation and $S_v O_2$ is the initial value of mixed venous oxygen saturation.

15. The method of claim 13 including the step of monitoring oxygen consumption of the patient from the calculated value of R and the carbon dioxide production.

16. The method of claim 15 including the step of displaying a value of oxygen consumption over time.

17. A method of continuously monitoring cardiac output of a patient comprising the steps of:
determining an initial value of cardiac output (Q) in volume per unit time of the patient by employing a first technique;
determining initial values of carbon dioxide production ($VCO_2$) in volume per unit time, percentage of arterial oxygen saturation ($S_a O_2$) and percentage of mixed venous oxygen saturation ($S_v O_2$) of the patient;
calculating a value for a constant k employing the initial values of Q, $VCO_2$, $S_a O_2$ and $S_v O_2$, where $k = VCO_2/(Q(S_a O_2 - S_v O_2))$;
thereafter continuously determining current values of $VCO_2$, $S_a O_2$ and $S_v O_2$; and
calculating a current value of Q employing the calculated value of k and the current values of $VCO_2$, $S_a O_2$ and $S_v O_2$, where $Q = VCO_2/(k(S_a O_2 - S_v O_2))$.

18. The method of claim 17 wherein the first technique is an indicator dilution technique.

19. The method of claim 18 wherein the indicator dilution technique is a thermodilution technique.

20. The method of claim 17 wherein the initial and current values of $VCO_2$ are determined by measuring the fractional concentration of $CO_2$ in gas expired by the patient and measuring the volume of gas expired by the patient.

21. The method of claim 17 wherein initial and current values of $S_a O_2$ are determined by employing an oximeter to measure values of $S_a O_2$.

22. The method of claim 17 wherein the initial and current values of $S_vO_2$ are determined by employing a fiberoptic right heart catheter to measure values of $S_vO_2$.

23. The method of claim 17 including the step of providing a fiberoptic right heart catheter for use in determining $S_vO_2$.

24. The method of claim 23 wherein the first technique is a thermodilution technique and wherein the catheter includes a thermistor which is employed for temperature sensing in conjunction with the thermodilution technique.

25. Apparatus for continuously determining cardiac output in volume per unit time of a patient comprising:
   first means for monitoring the volume of carbon dioxide expired by the patient per unit time and generating a first signal representing the current value thereof;
   second means for monitoring the arterial oxygen saturation of the patient and generating a second signal representative of the current value thereof;
   third means for monitoring the mixed venous oxygen saturation of the patient and providing a third signal representative of the current value thereof; and
   processing means for receiving the first, second and third values and (a) initially calculating a cardiac output constant as a function of at least one measured parameter of the patient without employing any assumed ratio between oxygen intake and carbon dioxide production for the patient and (b) thereafter calculating a current value of cardiac output of the patient as a function of the cardiac output constant and the current values of the first, second and third signals.

26. The apparatus of claim 25 wherein the processing means calculates current cardiac output substantially in accordance with the equation $Q = VCO_2/(k(S_aO_2 - S_vO_2))$, where Q is cardiac output, $VCO_2$ is volume of carbon dioxide expired by the patient per unit time, k is the calculated cardiac output constant of the patient, $S_aO_2$ is the current value of the arterial oxygen concentration of the patient and $S_vO_2$ is the current value of mixed venous oxygen concentration of the patient.

27. The apparatus of claim 25 wherein the third means is a fiberoptic right heart catheter.

28. The apparatus of claim 27 wherein the processing means calculates the cardiac output constant as a function of values of arterial and mixed venous concentrations of both carbon dioxide and oxygen obtained by analyzing blood samples of the patient.

29. The apparatus of claim 25 wherein the first means is comprised of flow measurement means to measure the flow of gas expired by the patient and analyzer means to measure the fractional concentration of carbon dioxide in gas expired by the patient.

30. The apparatus of claim 25 including display means which displays cardiac output as a function of time.

31. The apparatus of claim 30 wherein the processing means includes means for calculating a current value of oxygen transport of the patient and the display means displays the calculated values of oxygen transport over time.

32. The apparatus of claim 30 wherein the processing means includes means for calculating a current value of oxygen consumption of the patient and the display means displays the calculated values of oxygen consumption over time.

33. Apparatus for continuously determining cardiac output in volume per unit time of a patient comprising:
   first means for monitoring the volume of carbon dioxide expired by the patient per unit time and generating a first signal representing the current value thereof;
   second means for monitoring the arterial oxygen saturation of the patient and generating a second signal representative of the current value thereof;
   third means for monitoring the mixed venous oxygen saturation of the patient and providing a third signal representative of the current value thereof; and
   processing means for receiving the first, second and third values and (a) initially calculating a cardiac output constant as a function of at least one measured parameter of the patient, wherein the processing means calculates the cardiac output constant as a function of an initial measurement of cardiac output of the patient and initial values of the first, second and third signals and (b) thereafter calculating a current value of cardiac output of the patient as a function of the cardiac output constant and the current values of the first, second and third signals.

* * * * *